United States Patent
Salzer et al.

(10) Patent No.: US 10,126,246 B2
(45) Date of Patent: Nov. 13, 2018

(54) LAB-ON-A-CHIP FOR ALKALINITY ANALYSIS

(71) Applicant: Hach Company, Loveland, CO (US)

(72) Inventors: Corey Alan Salzer, Fort Collins, CO (US); Vishnu Vardhanan Rajasekharan, Fort Collins, CO (US); Isabel Nicola Huenig, Duesseldorf (DE); Rainer Froemel, Troisdorf (DE); Markus Lenhard, Viersen (DE); Rolf Dieter Uthemann, Leverkusen (DE); Aria Farjam, Duesseldorf (DE)

(73) Assignee: HACH COMPANY, Loveland, CO (US)

(*) Notice: Subject to any disclaimer, the term of this patent is extended or adjusted under 35 U.S.C. 154(b) by 130 days.

(21) Appl. No.: 14/918,178

(22) Filed: Oct. 20, 2015

(65) Prior Publication Data

US 2016/0041103 A1 Feb. 11, 2016

Related U.S. Application Data

(62) Division of application No. 13/187,635, filed on Jul. 21, 2011, now Pat. No. 9,182,353.

(60) Provisional application No. 61/399,989, filed on Jul. 22, 2010.

(51) Int. Cl.
| | |
|---|---|
| *G01N 21/78* | (2006.01) |
| *G01N 21/79* | (2006.01) |
| *G01N 21/80* | (2006.01) |
| *G01N 33/18* | (2006.01) |
| *G01N 21/77* | (2006.01) |

(52) U.S. Cl.
CPC ............ *G01N 21/78* (2013.01); *G01N 21/79* (2013.01); *G01N 21/80* (2013.01); *G01N 33/182* (2013.01); *G01N 2021/7763* (2013.01)

(58) Field of Classification Search
CPC .......... B01L 2300/0816; B01L 3/5027; B01L 2400/0415; B01L 2400/0487; B01L 2300/0867; B01L 3/502746; B01L 2300/0864; B01L 3/50273; B01L 3/502753; B01L 9/527; B01L 2400/0406; B01L 3/502715
See application file for complete search history.

(56) References Cited

U.S. PATENT DOCUMENTS

| | | | |
|---|---|---|---|
| 4,790,640 A * | 12/1988 | Nason | B01L 3/502707 156/99 |
| 5,710,372 A | 1/1998 | Becket | |
| 6,413,473 B1 | 7/2002 | Bacon | |
| 2005/0037508 A1* | 2/2005 | Hernandez | B01L 3/5027 436/163 |

(Continued)

OTHER PUBLICATIONS

Liu et al., "Passive Mixing in a Three-Dimensional Serpentine Microchannel", J. Microelectromechanical. Systems, 2000, v. 9, No. 2, pp. 190-197.*

(Continued)

*Primary Examiner* — Samuel P Siefke
(74) *Attorney, Agent, or Firm* — Ference & Associates LLC

(57) ABSTRACT

Described is a lab-on-a-chip device and a method of employing a lab-on-a-chip device for determining the concentration of species present in the water.

12 Claims, 14 Drawing Sheets

(56) References Cited

U.S. PATENT DOCUMENTS

2007/0092407 A1   4/2007  Xiao et al.
2007/0183930 A1*  8/2007  Roman ................ G01N 21/253
                                                422/82.05

OTHER PUBLICATIONS

European Patent Office, Supplmentary European Search Report for Application EP 11 80 9362, dated Feb. 16, 2016, 1 page, European Patent Office, Munich, Germany.

* cited by examiner

LOW ALKALINITY　　　　　　　HIGH ALKALINITY $$[AlK] \propto \frac{Abs_1}{Abs_2}$$

$$[AlK]^0 = \left(\frac{Abs_1'}{Abs_2'}\right) \times \text{Calibration}$$

$$AlK = A_c + [AlK]^0$$

$Abs_1$ = ABSORBANCE OF SAMPLE & BUFFER & INDICATOR $Abs_2$ = ABSORBANCE OF SAMPLE AFTER COMBINATION OF SAMPLE/BUFFER/INDICATOR REACTS WITH EXCESS BASE.

$Abs_1'$ = ABSORBANCE OF SAMPLE + STRONG ACID + B/I $Abs_2'$ = ABSORBANCE OF SAMPLE + STRONG ACID + EXCESS BASE

LAB-ON-A-CHIP FOR ALKALINITY ANALYSIS

CROSS REFERENCE TO RELATED APPLICATIONS

This application claims priority of U.S. Provisional Application No. 61/399,989, entitled "LAB ON A CHIP FOR ALKALINITY ANALYSIS," filed Jul. 22, 2010, and is a divisional application of U.S. application Ser. No. 13/187,635, entitled "LAB-ON-A-CHIP FOR ALKALINITY ANALYSIS," filed on Jul. 21, 2011, the contents of which are incorporated by reference herein.

FIELD

The invention relates to the detection of alkalinity in water.

BACKGROUND

Accurate alkalinity determinations are important to many industries and water types. For example, in drinking water, a high alkalinity can result in an objectionable taste. Alkalinity of water is the same as its acid-neutralizing capacity and is measured by the sum of all the titratable bases. Water may have a high alkalinity due to the presence of hydroxides, carbonates, bicarbonates, and other forms of oxidized carbon.

Alkalinity is a required reporting parameter for many regulatory agencies such as the EPA and FDA. The EPA has listed pH (which is a function of alkalinity) as a secondary drinking water regulation, limiting pH to 6.5-8.5. Alkalinity concentration is also used in industrial water discharge regulation. Per the EPA disinfection byproduct rule, industrial effluent alkalinity is controlled as alkalinity is increased or decreased based upon the Total Organic Carbon (TOC) concentration in the water—as TOC relates to the formation of trihalomethanes. Trihalomethanes can have adverse health effects, and the EPA limits the concentration of some trihalomethanes in drinking water to 80 parts per billion (ppb).

BRIEF SUMMARY

According to a second broad aspect of the present invention, there is provided a method comprising the following steps: (a) forcing an aqueous sample through a sample channel in a chip to mix the aqueous sample with one or more reagents located in one or more reagent zones of the sample channel and thereby forming a mixture that exhibits a color change due to the interaction of one or more reagents with a constituent of the aqueous sample and/or with a selected one or more of the one or more reagents, (b) measuring a color change in the mixture in an optical pathway in the sample channel, and (c) displaying data on a visual display device based on the color change measured in step (b).

BRIEF DESCRIPTION OF THE SEVERAL VIEWS OF THE DRAWINGS

The accompanying drawings illustrate exemplary embodiments of the present invention and, together with the general description given above and the detailed description given below, serve to explain the features of the present invention. The figures are not necessarily to scale, and some features may be exaggerated to show details of particular components. Therefore, specific details disclosed herein are not to be interpreted as limiting, but merely as a basis for the claims and as a representative basis for teaching one skilled in the art to variously employ the present invention. As a result, the present invention is not limited to the specific examples described below, but only by the claims and their equivalents.

FIG. 13 shows a method of calculating the alkalinity as a means of absorbance according to one embodiment of the present invention.

DETAILED DESCRIPTION

Definitions

Figure 1:
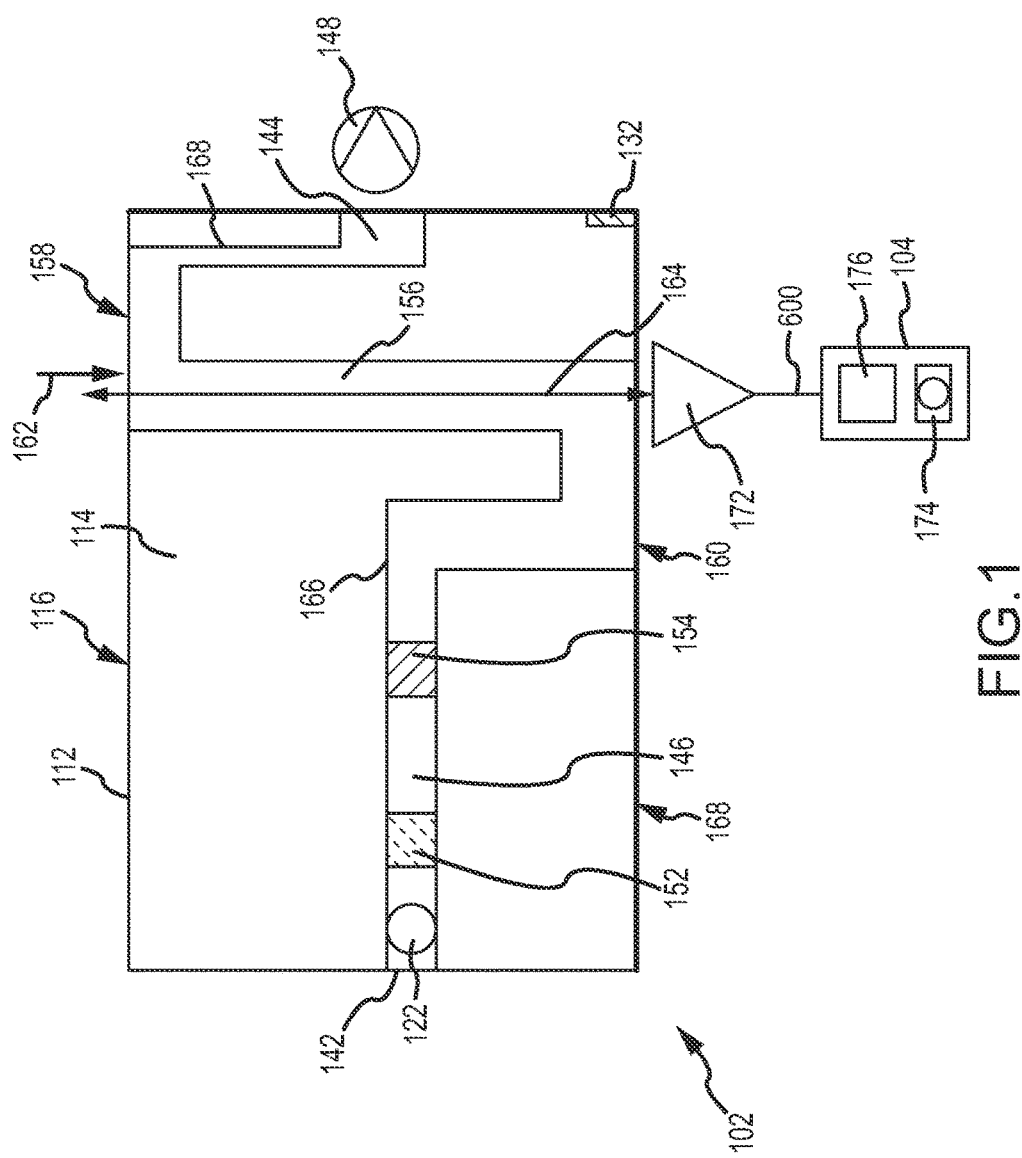
FIG. 1 is a schematic drawing of a high-range alkalinity lab-on-a-chip device and portable reader according to one embodiment of the present invention.

Where the definition of a term departs from the commonly used meaning of the term, applicant intends to utilize the definition provided below, unless specifically indicated.

For purposes of the present invention, it should be noted that the singular forms "a," "an," and "the" include reference to the plural unless the context as herein presented clearly indicates otherwise.

For purposes of the present invention, directional terms such as "top," "bottom," "upper," "lower," "above," "below," "left," "right," "horizontal," "vertical," "up," "down," etc., are used merely for convenience in describing the various embodiments of the present invention. The embodiments of the present invention may be oriented in various ways. For example, the diagrams, devices, etc., shown in the drawing figures may be flipped over, rotated by 90.degree. in any direction, reversed, etc. For example, rows and/or columns may be oriented in any direction.

For purposes of the present invention, a value or property is "based" on a particular value, property, the satisfaction of a condition, or other factor, if that value is derived by performing a mathematical calculation or logical decision using that value, property or other factor.

For purposes of the present invention, the term "Alkalinity" and "$A_T$" refers to a measurement of the ability of a solution to neutralize acids to the equivalence point of carbonate or bicarbonate. The alkalinity is equal to the stoichiometric sum of the bases in solution. In the natural environment carbonate alkalinity tends to make up most of the total alkalinity due to the common occurrence and dissolution of carbonate rocks and presence of carbon dioxide in the atmosphere. Other common natural components that may contribute to alkalinity include borate, hydroxide, phosphate, silicate, nitrate, dissolved ammonia, the conjugate bases of some organic acids and sulfide. Solutions produced in a laboratory may contain a virtually limitless number of bases that contribute to alkalinity. Alkalinity is usually given in the unit mEq/L (milliequivalent per liter). Commercially, as in the pool industry, alkalinity may also be given in the unit "ppm," or parts per million. Alkalinity is sometimes incorrectly used interchangeably with basicity. For example, the pH of a solution can be lowered by the addition of $CO_2$. This will reduce the basicity; however, the alkalinity will remain unchanged.

For purposes of the present invention, the term "analysis report" refers to any organized presentation of data, raw data or historical data, manipulated data, observational data, information, analysis result, etc., based on data obtained by one or more chip readers taking readings from one or more lab-on-a-chip devices for one or more samples. An analysis report may be generated or manipulated by an analyzer that is part of the chip reader and/or server. An analysis report may be prepared for any intended recipient, such as an elected official, manager or operator of a water treatment system, customer, member of the public, etc. According to some embodiments of the present invention, an "analysis report" may be a submission to a regulatory and/or law enforcement agency in any required format.

For purposes of the present invention, the term "analysis result" refers to any information, value, relationship, product, etc., created by aggregation, calculation, algorithm, analysis, manipulation, etc., of data or information obtained or collected from one or more lab-on-a-chip devices as performed by an analyzer on a chip reader and/or the server of a remote water quality monitoring system. For example, an "analysis result" may include observational data analyzed, manipulated, etc., by a chip reader.

For purposes of the present invention, the term "analyte" refers to a constituent of an aqueous sample that is being analyzed by a lab-on-a-chip device, chip reader, or user.

For purposes of the present invention, the term "analyzer" refers to a portion of a chip reader, server, output device, visual display device, or other device in which may be stored one or more software program(s) or other routine(s), firmware and/or hardware, which may analyze, manipulate, etc., data such as raw data, observational data, historical data or any other information obtained from one or more lab-on-a-chip devices. According to some embodiments of the present invention, an analyzer may analyze or manipulate the data to generate the output. The analyzer may comprise a source code or a software program. According to some embodiments of the present invention, the analyzer may compare the data continuously, in real-time, at periodic or selected intervals, on condition or on demand by a user. According to some embodiments of the present invention, the output may comprise one or more of the following: data, alarm, analysis result or analysis report.

For purposes of the present invention, the term "aqueous sample" refers to a sample that contains water. In various embodiments of the present invention aqueous samples to be analyzed may obtained by dipping a lab-on-a-chip device in a water source and then using suction from a pump or capillary action to pull the aqueous sample into a sample channel of the lab-on-a-chip device.

For purposes of the present invention "chip" refers to a portable device having at least one channel therein into which a liquid sample may be placed. In some embodiments, a chip may have an inlet that allows a sample to be inserted into a channel in the chip via capillary action or via the use of a pump to either push or pull the sample into the chip. Although in the embodiments shown in the drawings, the chips are rectangular and box-like in shape, a chip may have any shape. In some embodiments, a chip is small enough to be inserted into a chip reader. A chip may include various subcomponents to take or facilitate measurements of an aqueous sample and provide or interact with other components of a system. A chip may have multiple channels to allow multiple samples to be analyzed.

For purposes of the present invention, the term "color shifting agent" refers to a reagent that is added to a mixture of an aqueous sample and an indicator for the purpose of shifting the color of the indicator.

For purposes of the present invention, the term "communication link" refers to any suitable technology for sending, uploading or communicating an output, including data, information, analysis results, analysis reports, alerts, alarms, etc., between two devices such as a chip reader and a server, a server and a visual display device, etc. For example, according to some embodiments of the present invention, a suitable technology to serve as a "communication link" may be the Internet or World Wide Web. In such a case, the output may be uploaded onto an Internet server computer, which may be the server of the present remote water quality monitoring system, or the Internet server computer may be separate from the server. According to other embodiments, the "communication link" for sending an output to, or allowing access to an output by, a remote viewing device, includes, but is not limited to, any wired or wireless connections as well as any protocols: the Internet; TCP/IP; MODBUS RTU; MODBUS ASCII and MODBUS TCP; XML; Ethernet; file transfer protocol (FTP); BLUETOOTH; ZIGBEE; email; such as SMTP; cellular phone networks; such as CDMA and TDMA; radio signals or remote terminal units (RTU) coupled to radio frequency transmitters; cellular modems; SDI-12; satellite transmissions; existing telephone or communication networks or wiring; a standard public switched telephone network (PSTN); dial-up using landline or telephone; a wireless network such as wi-fi; a wide area network (WAN); a wireless local area network (WLAN); a local area network (LAN) or metropolitan area network (MAN); a cable Internet connection; a short message system (SMS); dial-up modem; a point-to-point link; a global system for mobile communications (GSM, 3GSM); general packet radio services (GPRS); evolution-data optimized (EV-DO); enhanced data rates for GSM evolution (EDGE); digital enhanced cordless telecommunications (DECT); integrated digital enhanced network (iDEN); universal mobile telecommunications systems (UMTS) or advanced mobile phone systems (AMPS); or any other suitable means known to those skilled in the art to send, upload or communicate an output to a remote viewing device.

For purposes of the present invention, the term "constituent" refers to anything such as a substance, ion, etc. present in an aqueous sample other than pure water. Examples of constituents include hydronium ions, hydroxide ions, metal ions, dirt, bacteria, etc.

For purposes of the present invention, the term "data" refers to any information, reading, measurement, value, etc., ultimately obtained by one or more chip readers reading one or more lab-on-a-chip devices for one or more samples or any information, reading, measurement, value, etc., derived from such data. The term "data" includes any data or information including raw data obtained directly by the one or more chip readers without manipulation, historical data earlier obtained from one or more chip readers or entered or derived from data obtained at an earlier point or period in time, and analyzed or manipulated data, such as data or information manipulated, analyzed, etc.

For purposes of the present invention, the term "database" refers to a device or devices used to store data, raw data, historical data, manipulated data and/or information in a logical or ordered arrangement or configuration. The database may be either part of the server or separate from the server, albeit connected to or in communication with the server.

For purposes of the present invention, the term "distant" in reference to a server and/or server database refers to the server and/or server database being physically separated from an environmental instrument or remote user. The term "distant" may refer to a server and/or server database that is connected or linked to one or more environmental instruments and one or more remote users only via a wireless communication system.

For purposes of the present invention, the term "environmental data" refers to data obtained by a chip reader from reading lab-on-a-chip devices for one or more samples that relates to the environment or changes to the environment of a location from which an aqueous sample for a lab-on-a-chip has been obtained.

For purposes of the present invention, the term "gas opening" refers to an opening in a channel of a chip that may be used by a pump to pull a gas, such as air, from a channel or to push a gas, such as air, into a channel. In at least some embodiments, a gas opening is sufficiently small that a sample cannot exit a chip through the gas opening. By pulling a gas from a channel through a gas opening, a pump may pull a liquid sample through the channel from the sample inlet of the channel. By pushing a gas into a channel through a gas opening, a pump may drive a sample through a channel in a chip. In some embodiments, a sample inlet may function as a gas opening allowing a sample to be pushed through the channel of a chip by a pump. The gas that is pulled or pushed through a gas opening may be air or an inert gas such as nitrogen or a noble gas.

For purposes of the present invention, the term "hardware and/or software" refers to functions that may be performed by digital software, digital hardware or a combination of both digital hardware and digital software. For example, a "program" may be a software program, a program that is part of the digital hardware of a computer or environmental instrument, or a combination of both digital hardware and digital software.

For purposes of the present invention, the term "indicator" refers to a compound or a mixture of compounds that changes color in response to a reaction. An example of an indicator is a pH indicator that changes color in response to a change in pH. An indicator may be a combination of compounds. For example, an indicator may be a pH indicator system comprising bromocresol green and methyl red.

For purposes of the present invention, the term "inlet" refers to the open end of a channel that allows water and other fluids to enter the channel.

For purposes of the present invention, the term "interactive visual display device" refers to a visual display device that a user may interact with by means of an input device. The input device may be a touchscreen of the visual display device, a touchpad, a mouse, a trackball, a keyboard, etc. Examples of interactive visual display devices include a computer with a monitor, a laptop computer, a tablet computer, a cellphone, a smartphone, etc.

For purposes of the present invention, the term "logger" or "data logger" refers to a device that records data. An example of a logger is a water flow logger that records the water flow of a water source.

For purposes of the present invention, the term "observational data" refers to data or information that has been analyzed, manipulated, etc., by a chip reader, from raw data or information obtained by the chip reader from reading one or more lab-on-a-chip devices for one or more samples prior to being transmitted to a server and/or server database.

For purposes of the present invention, the term "optical pathway" refers to a pathway that allows light to (1) enter a channel of a chip, (2) exit the channel of the chip and (3) interact with samples, reagents, etc. in the optical pathway between entering and exiting the channel of the chip. In some embodiments of the present invention, an optical pathway may include two windows that allow light to enter a channel through one window and exit the channel through the other window. In some embodiments of the present invention, the optical pathway may include a window and one or more mirrors so that light is allowed to enter the channel through the window and the be reflected back along the optical path by the one or more mirrors so that the light eventually exits the channel through the window.

For purposes of the present invention, the term "output" refers to any product, publication, submission, uploaded content, etc., including any information, data, analysis result, analysis report, etc., that may be communicated from the server of the present remote water quality monitoring system to a remote viewing device in a format suitable for display by the remote viewing device to a user.

For purposes of the present invention, the term "output device" refers to any device or apparatus known in the art that may be used by a user to view or that makes a user aware of the results of a chip reader reading a lab-on-a-chip device for a sample, such as, for example, the chip reader itself, a personal computer or a terminal, a server, etc., as well as a variety of handheld personal communications equipment, such as a cellphone, a pager, a PDA, a smartphone, a BLACKBERRY, a PALM device, an IPHONE, etc.

For purposes of the present invention, the term "processor" refers to a single processing device or a group of interoperational processing devices. Some examples of processors are computers, integrated circuits, logic circuitry, etc.

For purposes of the present invention, the term "reagent zone" refers to a portion of a sample channel of a lab-on-a-chip device where reagents are held in place to react with the sample as the sample passes through the reagent zone. Reagents such as acids, bases, indicators and buffers may be held in place in a reagent zone mechanically through structures via physical adhesion or chemical bonding (dipoledipole, hydrogen bonding, covalent bonding, salt, etc.), and also by surface tension, encapsulated, freeze-dried, etc.

For purposes of the present invention, the term "remote" refers to any location that is removed from the location of the initial sample analysis location.

For purposes of the present invention, the term "remote user" refers to a user that is remote from one or more environmental instruments of a water quality monitoring system according to an embodiment of the present invention.

For purposes of the present invention, the term "server" refers to the conventional meaning of the term "server" with respect to a computer network, i.e., a server is one or more computers that make services such as access to data files, programs, peripheral services, etc. available to other devices on a computer network. A server may communicate with lab-on-a chip devices, output devices, visual display devices, etc. and provide a link between such devices. A "server" may be a web or Internet server. The "server" may include a database and/or an analyzer.

For purposes of the present invention, the term "server database" refers to a device or apparatus used to store data, raw data, historical data, manipulated data and/or information, such as in a logical or ordered arrangement or configuration. The server database may be part of the server or separate, albeit connected to or in communication with the server. As such, the "server database" is physically separated, i.e., at a remote or distant location, from the location of the environmental instruments and the remote users of a remote water quality monitoring system.

For purposes of the present invention, the term "transmission interface" refers to a portion of a chip reader that is capable of transmitting data or information to a server via any suitable wireless communication link.

For purposes of the present invention, the terms "treat," "treated," "treating," "treatment" and the like shall refer to any process, treatment, generation, production, discharge or other operation that may be performed by a water treatment system on, or in relation to, the water in the water treatment system.

For purposes of the present invention, the term "user" refers to a person, entity or agency that views data, information, analysis results or analysis reports communicated from the server to the remote viewing device of the present remote water quality monitoring system.

For purposes of the present invention, the terms "visual display device" and "visual display apparatus" include any type of visual display device or apparatus such as a chip reader, CRT monitor, LCD screen, LEDs, projected display, printer for printing out an image such as a picture and/or text, etc. A visual display device may be a part of another device such as a computer monitor, television, projector, cellphone, smartphone, laptop computer, tablet computer, handheld music and/or video player, personal data assistant (PDA), handheld game player, head-mounted display, heads-up display (HUD), global positioning system (GPS) receiver, automotive navigation system, dashboard, watch, microwave oven, automated teller machine (ATM), etc. A visual display device is one type of output device.

For purposes of the present invention, the term "water" refers to any type of water found in nature, contaminated or uncontaminated by pollutants, and water or any fluid that may be processed, treated, generated, produced, discharged, etc., by a water treatment system. For example, the term "water" may refer to water being treated or processed by a water treatment facility for the distribution of potable drinking water to the public, or the term "water" may refer to sewage or wastewater processed or treated by a central wastewater treatment plant (WWTP). Thus, "water" may include any number of solutes, sediments, suspensions, organic matter, etc., as the case may be.

For purposes of the present invention, the term "water source" refers to any source of water, either natural or manmade. Examples of water sources include oceans, gulfs, bays, lakes, rivers, streams, creeks, reservoirs, sewers, water tanks, water pipes, etc.

For purposes of the present invention, the term "water stream" refers to any flow of water. Examples of water streams include natural flows of water such as a creek, stream, river, etc., or flows of water in a manmade conduit such as a canal, pipe, sewer, faucet, spigot., stand-pipe, well, aqueduct, etc.

For purposes of the present invention, the term "web server" and "Internet server" refer to the conventional meaning of those terms, i.e., a computer that helps deliver content to another computer, a user, a visual display device, etc., that may be accessed through the Internet.

Description

Accurate monitoring of water alkalinity in drinking water and industrial applications is important. Traditionally, alkalinity is measured by titration with a strong acid titrant using colorimetric or potentiometric endpoint detection. In recent years, the manual titration process has been automated. For example, the Hach Company APA 6000 analyzer provides alkalinity measurements via a sequential injection analyzer.

Figure 5:
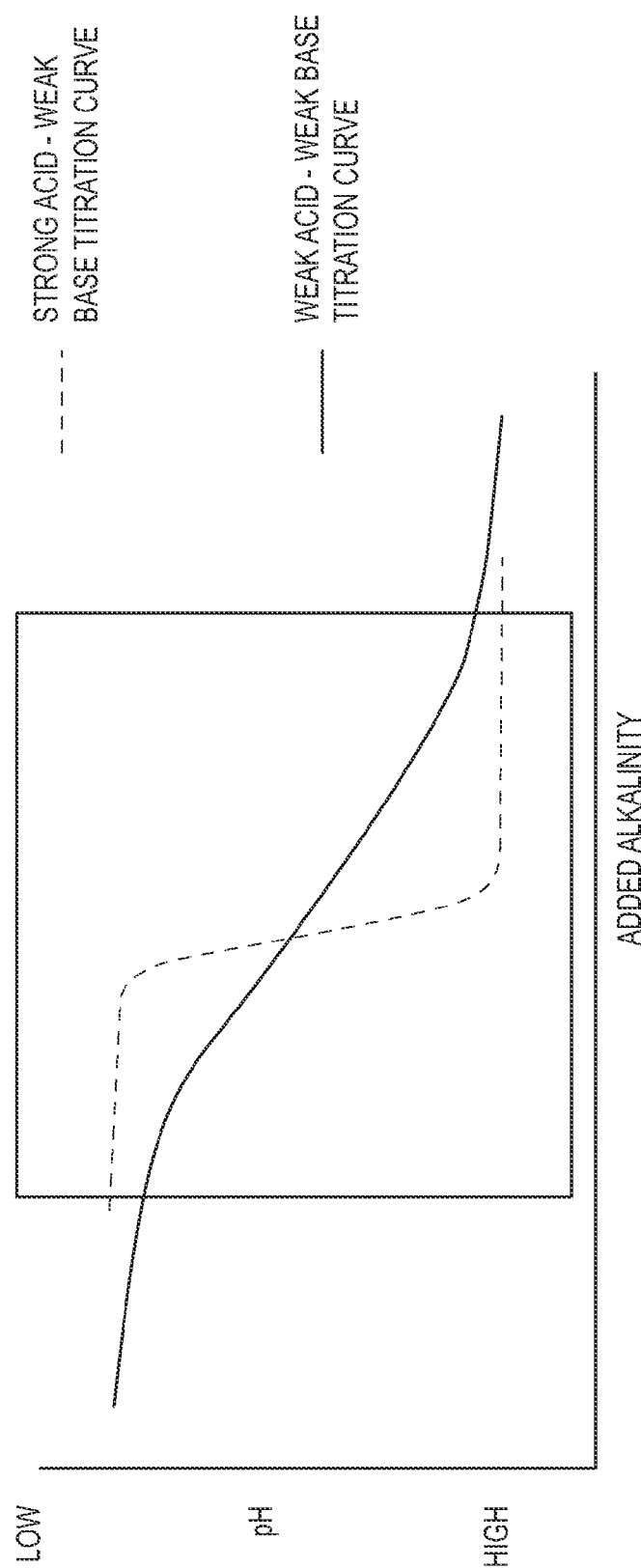
FIG. 5 is a graphical representation of the impact on a buffered color indicator with increasing alkalinity in a sample in contrast with the change noted with a traditional strong acid titration.

An example of the traditional alkalinity titration is described in "General Chemistry Principles and Modern Applications," Ralph H. Petrucci and William S. Hardwood, 6.sup.th Ed., New York, pp. 155-61 (1993). Petrucci et al. describes a titration in the presence of phenolphthalein whereby the endpoint is detected by a color change of the solution. A traditional strong acid titration for alkalinity determination typically involves the addition of a strong acid of known concentration, such as 0.02N sulfuric acid, to a known volume of a sample. The sample has added to it a small amount of color indicator that has a color transition at a specific pH. This is known as the endpoint of the titration. The color transition is desired to occur over a narrow pH range. Examples of such indicators include phenolphthalein and bromocresol green. FIG. 5 shows a general titration curve for a strong acid titration for alkalinity. The volume and concentration of the added strong acid added up to the end point and the known volume of sample is used for the determination of the alkalinity in the sample based on the following equation:

Conc. of Alkalinity=(Conc. of acid)×(Vol. of Added Acid)/(Vol. of Alkalinity Sample).

A traditional alkalinity titration method is described in the "2320 Alkalinity" section of the American Public Health Association's publication Standard Methods (2005). In this method the alkalinity of a sample is determined by addition of an acid to a solution until a desired end point pH is achieved. Thereby the concentration of alkalinity is determined by the amount of acid needed to reach the endpoint. Also disclosed, among other things, is use of a color indicator in the absence of an interfering color and turbidity.

In recent years manual measurements have been automated. For example, a microprocessor-controlled process analyzer designed to continuously monitor a sample water stream for alkalinity is described in the Hach Company APA 6000. Alkalinity 2001 Operation Manual. The analyzer provides concentrations of total alkalinity, phenolphthalein, hydroxide, carbonate, and bicarbonate alkalinity in the sample stream. This instrument uses an automated colorimetric titration method to determine alkalinity concentration and can operate up to 30 days without human interaction.

European Patent Application No. 1506813 Hernandez et al., entitled "Microfluidic titration apparatus" published Feb. 16, 2005, describes determining alkalinity by means of a micro-fluidic chip titration. Hernandez et al. describes an analytical titration chip that includes a plurality of microfluidic sample channels that fluidly communicate with plural titration chambers. Each titration chamber contains a different concentration of the same titrant to define a range of titrations. The fluid travels through the microfluidic channels by means of capillary action. The entire contents and disclosure of this European patent application are incorporated herein by reference.

U.S. Pat. No. 5,844,686 to Treptow et al., entitled "System for pipetting and photometrically evaluation samples," issued Dec. 1, 1998, describes a system for pipetting and photometrically evaluating samples. Treptow describes a hand apparatus that comprises a pipetting means, an integrated photometer and a replaceable pipette tip connected to the pipetting means, where the pipette tip is a cell within an optical pathway of the photometer, allows for photometrically evaluating absorbed samples. The entire contents and disclosure of this patent are incorporated herein by reference.

U.S. Pat. No. 7,459,713 to Coates, entitled "Integrated sensing system approach for handheld spectral measurements having a disposable sample handling apparatus," issued Dec. 2, 2008, describes an integrated sensing system approach for handheld spectral measurements having a disposable sample handling apparatus. Here, an integrated sensing engine is described featuring energy sources and detectors within a single package that includes sample interfacing optics, acquisition and processing electronics. The sensor's response covers the range of 200 nm to 25 nm based on solid-state detectors. The sample is drawn into the measurement region of the sensing device via a pump or suction device where the sample reacts with the reagents whereby a reading of the optical properties of the sample and reagents can be conducted. The entire contents and disclosure of this patent are incorporated herein by reference.

U.S. Pat. No. 7,491,366 to Tokhtuev et al., entitled "Portable multi-channel device for optically testing a liquid sample," issued Feb. 17, 2009, describes a portable multi-channel device for optically testing a liquid sample. A multi-channel portable device is described that allows for the detection of turbidity and other water parameters. The entire contents and disclosure of this patent are incorporated herein by reference U.S. Patent Application No. 2008/0265146 to Coates, entitled "Integrated sensing module for handheld spectral measurements" describes a miniaturized integrated spectral sensor, with integrated sensed signal conditioning, signal exchange, and integration into a handheld device for the measurement of solution and solvent-based chemistries. The sensed information is converted into concentrations and mixtures of specified species. The entire contents and disclosures of this patent application are incorporated herein by reference.

In one embodiment, the present invention provides a method that may be used to accurately determine the concentration of alkalinity in an aqueous sample on a chip that interfaces with an instrument for colorimetric analysis and fluid control.

In one embodiment, the present invention provides a lab-on-a-chip device for the measurement of alkalinity comprising a chip configured to include one or more sample channels. Each sample channel includes an inlet, one or more reagent zones including one or more reagents and one or more optical pathways. In some embodiments of the present invention, the lab-on-a-chip device may include a pump for causing fluid to flow through the sample channel. The lab-on-a-chip device is configured to interface with: (1) at least one optical system that can record the sample color, (2) at least one reader that contains at least one computer, (3) at least one visual display device and (4) at least one set of controls.

In another embodiment, the present invention provides a method employing lab-on-a-chip technology to analyze alkalinity in a sample. The method comprises exposing one or more chips configured to include one or more sample inlets to a sample. Each of the chips is concurrently or subsequently attached to the optical system. The sample travels along one or more sample channels as a result of force provided by one or more pumps that are part of a chip reader or part of the chip. As the sample travels along the sample channel, the sample encounters one or more reagents, and then one or more optical pathways. The optical system records the sample color and the sample color is transmitted to a reader. The reader transmits the data to a visual display device where it is displayed to a user. The lab-on-a-chip is configured to interface with one set of controls.

In one embodiment of the present invention, the lab-on-a-chip device is designed for intuitive and easy operation.

The reagents may include indicators, buffers, strong acids, acids and/or bases, and various other types of reagents. The reagents may be dry, dehydrated, liquid, and/or gels. In some embodiments, the reagents may be a mixture of phases.

In one embodiment of the present invention, the optical system of the lab-on-a-chip device may be connected to the reader via a solid physical connection or via a wireless connection.

In one embodiment of the present invention, the chip and the reader may be connected to the visual display device and the controls via a solid physical connection or via a wireless connection.

In one embodiment of the present invention, a first reagent added to the sample may be used to consume a known amount of analyte in the sample so as to modify the range of analyte determination.

In one embodiment of the present invention, the last reagent added to the sample may be used for the purpose of shifting the color of the indicator reagent(s) in the sample.

In one embodiment of the present invention, the use of a continuous color transition gradient may be employed for the purpose of determination of alkalinity.

FIGS. 1, 2, 3, 4, 5, 6, 7, 8, 9, 10, 11, 12, 13, 14 and 15 and the following detailed description of the present invention are disclosed herein; however, it is to be understood that the disclosed embodiments are merely exemplary of the present invention that may be embodied in various forms. The figures are not necessarily to scale, and some features may be exaggerated to show details of particular components. Therefore, specific details disclosed herein are not to be interpreted as limiting, but merely as a basis for the claims and as a representative basis for teaching one skilled in the art to variously employ the present invention. As a result, the present invention is not limited to the specific examples described below, but only by the claims and their equivalents.

FIG. 1 shows a lab-on-a-chip device 102 and a portable chip reader 104 according to one embodiment of the present invention. Lab-on-a-chip device 102 includes a chip 112 having a chip body 114 and two transparent walls, i.e., walls 116 and 118, on either side of chip body 114. Lab-on-a-chip device 102 includes various components used in measuring alkalinity in an aqueous sample, such as aqueous sample 122. When chip 112 is inserted into chip reader 104 an indent 132, i.e., an alignment interface of chip 112, interacts with a chip holding interface (not shown) of chip reader 104 to hold chip 112 in chip reader 104 when force is no longer applied to chip 112 by a user. Chip 112 has a sample inlet 142 and a gas opening 144. A sample channel 146 extends between sample inlet 142 and gas opening 144. Sample 122 is pulled through sample channel 146 via force exerted by a pump 148 that is part of chip reader or a part of the chip 104. Pump 148 exerts a suction force on sample 122 by pulling air from sample channel 146 via gas opening 144. As the sample 122 moves along the sample channel 146, sample 122 mixes with various reagents in reagent zones 152 and 154. Reagent zone 152 includes an acid 152. Reagent zone 154 includes an indicator and a buffer. Sample 122 may be pulled into sample channel 146 from a water source via capillary action or by using a pump on gas opening 144 when chip 112 is dipped into a water source or otherwise exposed to a water source.

Sample 122 reacts with the reagents in reagent zones 152 and 154 as sample 122 travels along sample channel 146. Sample channel 146 includes optical pathway 156 and two transparent windows 158 and 160 that allow light, shown by arrow 162 from chip reader 104 to traverse optical pathway 156 as shown by double-headed arrow 164. Sample channel 146 also includes a pre-optical pathway portion 166 and a post-optical pathway portion 168. Although for simplicity of illustration, pre-optical pathway portion 166 and post-optical pathway portion 168 are shown in FIG. 1 as having only one (1) and two (2) bends, respectively, pre-optical pathway portion 166 and post-optical pathway portion 168 may have each several bends or other channel structures/undulations.

By directing light 158 through optical pathway 156, optical system 170 of chip reader 104 is able to measure the color of sample 122 and/or one or more of the reagents. When chip 102 is inserted into chip reader 104 the chip holding interface of the chip reader holds the chip in place and aligns optical pathway 156 with optical system 172 of chip reader 104. Optical system 170 transmits the color of sample 122 and/or one or more of the reagents electronically to chip reader 104 via a communication link 172. Chip reader 104 includes controls 174 and a display 176.

In one embodiment of the present invention, window 158 of FIG. 1 may be replaced with a mirror or a mirrored wall. In this embodiment, chip reader 104 may emit a light along optical pathway 156 that is reflected back into chip reader 104 by the mirror or mirrored wall.

The optical system of the chip reader measures the color ($Abs_1$) of the sample as the sample and reagents travel along the optical pathway. The alkalinity is proportional to the absorbance ($Abs_1$) as shown by Equation 1 below:

[Alkalinity]=($Abs_1$)×(Calibration Factor)

$$[Alkalinity] = ax^2 + bx + c \quad \text{(Equation 1)}$$

where, x=Absorbance

Although for simplicity of illustration only one indicator, one acid and one buffer are shown in FIG. 1, the sample channel may include multiple indicators, acids and buffers.

In one embodiment of the present invention, the chip reader includes hardware and/or software capable of converting the signal/data obtained by the optical system to an image that can be understood by the user on the display of the chip reader. In addition, the chip reader may include an analyzer capable of comparing the data to known guidelines and respond accordingly. For instance, a user could program the reader to send a shut-off alarm to a specific control valve if the alkalinity, or other parameter, exceeds a specific value. In one embodiment of the present invention, the chip reader may be pre-programmed to instruct the user to take additional readings if the alkalinity, or other parameter, is out of specified range. The chip reader may include hardware and/or software that are capable of performing any tasks of a portable computer, smartphone, etc.

In one embodiment of the present invention, the lab-on-a-chip device may be inserted into a handheld reader that houses the optical system. Based on the color of the sample and/or one or more of the reagents measured by the optical system, data is displayed on the display of the handheld reader. In this embodiment of the present invention, the communications link between the optical system and the display may be a wired communication link.

In one embodiment of the present invention, the communication link between the optical system of the chip reader and the visual display device that displays the data obtained by the optical system to the user may be a wireless communication link. For example, the lab-on-a-chip device may be inserted into a chip reader and then the chip reader sends a wireless signal to a visual display device or output device, such as a mobile phone or remote computer that has controls and a display.

In one embodiment of the present invention, the controls and display of the chip reader may be part of a cellphone. In one embodiment of the present invention, the controls and display may be a remote computer connected to a server that is then connected via a wired or wireless communication linked to the chip reader.

The use of the lab-on-a-chip device simplifies water quality measurements by incorporating elements of the measurement process such as fluid handling, reagent mixing and optical measurement onto a microfluidic platform. Additionally, the lab-on-a-chip device of the present invention may incorporate various reagents and procedures that can enhance the accuracy of water quality measurements while being transparent to the user.

The chip and the reader of the present invention can have a variety of shapes and sizes.

A variety of known interface combinations may be employed for holding and aligning a chip in the chip reader. For example, alignment pins, indents, springs, magnetic, bearings, etc. may be included on as an alignment interface on the chip and/or on the chip holding interface of the chip reader to allow the chip to be held in place in the chip reader and so that the optical pathway of the chip is alignment with the optical system of the chip reader.

Figure 2:
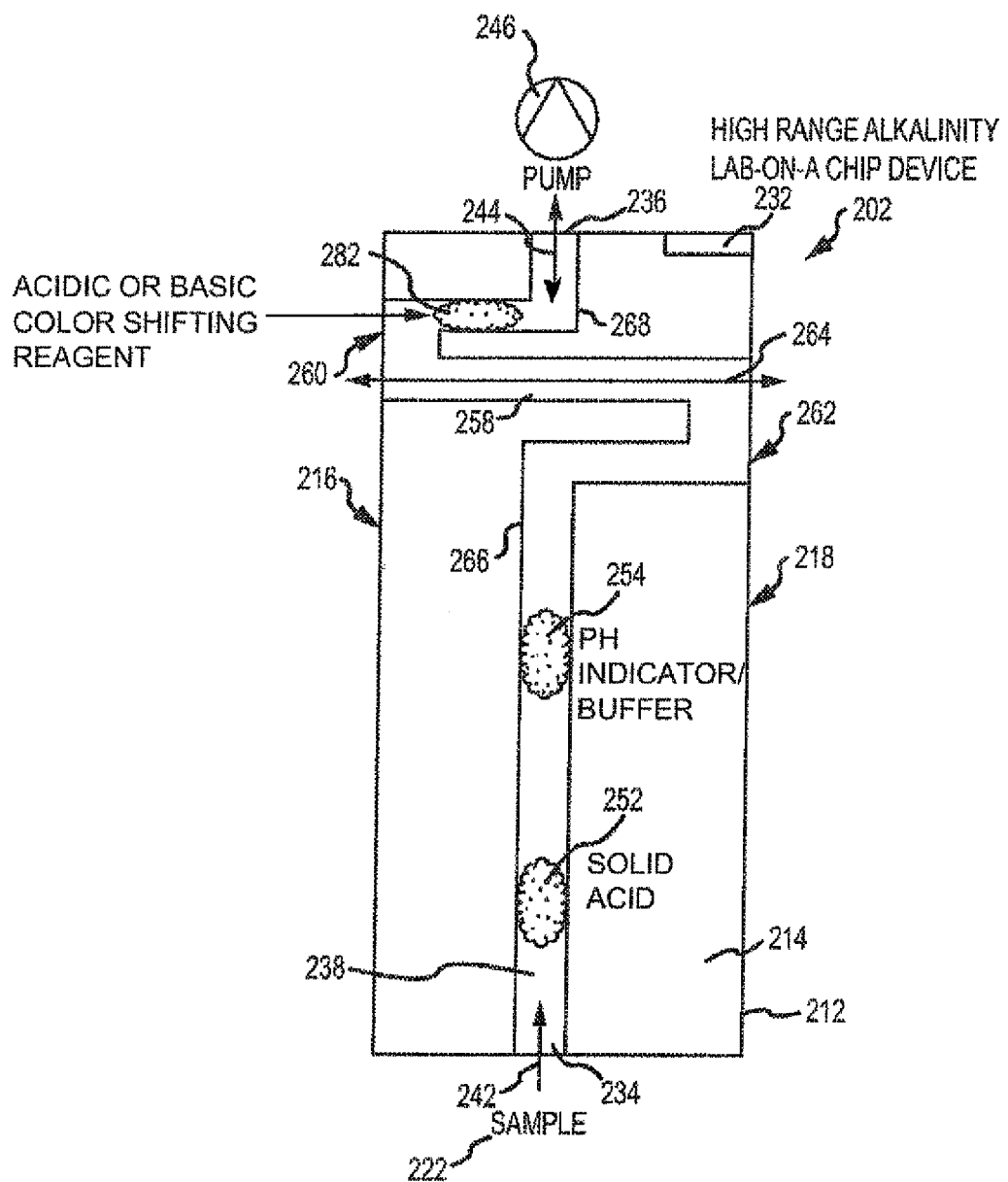
FIG. 2 is a schematic drawing of a high-range alkalinity lab-on-a-chip device according to one embodiment of the present invention.

FIG. 2 shows a high range alkalinity lab-on-a-chip device 202 according to one embodiment of the present invention. Lab-on-a-chip device 202 includes a chip 212 having a chip body 214 and two transparent walls, i.e., walls 216 and 218, on either side of chip body 214. Lab-on-a-chip device 202 includes various components used in measuring alkalinity in an aqueous sample, such as aqueous sample 222. When chip 212 is inserted into a chip reader (not shown), an indent 232, i.e., an alignment interface of chip 212, interacts with a chip holding interface (not shown) of the chip reader to hold chip 212 in the chip reader when force is no longer applied to chip 212 by a user. When chip 202 is inserted into the chip reader, indent 232 aligns the optical pathway with the optical system of the chip reader. Chip 212 has a sample inlet 234 and a gas opening 236. A sample channel 238 extends between sample inlet 234 and gas opening 236. Sample channel 238 includes optical pathway 258 and two transparent windows 260 and 262 that allow light from a chip reader reading chip 212 to traverse optical pathway 258 as shown by double-headed arrow 264. Sample channel 238 also includes a pre-optical pathway portion 266 and a post-optical pathway portion 268. Although for simplicity of illustration, pre-optical pathway portion 266 and post-optical pathway portion 268 are shown in FIG. 2 as having only one (1) and two (2) bends, respectively, pre-optical pathway portion 266 and post optical pathway portion 268 may each have several bends. Sample 222 may be pulled into sample channel 238 from a water source via capillary action or by using a pump on gas opening 236 when chip 212 is dipped into a water source or otherwise exposed to a water source. Sample 222 is pulled through sample channel 238, as indicated by arrows 242 and 244 via force exerted by a pump 246 that is part of the chip reader (not shown). Pump 246 exerts a suction force on sample 222 by pulling air from sample channel 238 via gas opening 236.

As the sample 222 is pulled through sample channel 238 by pump 246, sample 222 mixes with various reagents in reagent zones 252 and 254. Reagent zone 252 includes a strong acid. Reagent zone 254 includes an indicator and a buffer. Sample 222 reacts with the reagents in reagent zones 252 and 254 as sample 222 travels along sample channel 238.

Optical pathway 258 allows for the optical system of a chip reader, such as the chip reader of FIG. 1 (not shown in FIG. 2) to measure the color of sample 222 and/or one or more of the reagents. Then sample 222 undergoes an alkalinity test, in which sample 222 mixes a color shifting agent in reagent zone 282. The color reagent may be an acid or a base. The pumping of sample 222 through sample channel 238 may be stopped and/or the direction of pumping reversed to allow absorbance to be measured in optical pathway 258 by the chip reader after sample 222 mixes with the color shifting agent in reagent zone 282. The chip reader then displays the results to a user on a display.

In the embodiment of the invention shown in FIG. 2, there are two transparent windows, i.e., transparent windows 260 and 262 at either end of optical pathway 258. In this embodiment, light from the chip reader is directed through window 260 and the characteristics of the light are measured by the optical system of the chip reader when the light exits window 262. In another embodiment of the present invention, window 260 of FIG. 2 may be replaced with a mirror or a mirrored wall. In this embodiment, the chip reader may emit a light through window 262 along optical pathway 258 that is reflected back by the mirror or mirrored wall back along pathway and back through window 262 and into the optical system of the chip reader.

Although for simplicity of illustration in FIG. 2 only one sample channel with an associated sample inlet, gas opening, and pump are shown for each lab-on-a-chip device, a lab-on-a-chip device may have multiple sample channels. This may be accomplished by stacking multiple chips of the type shown in FIG. 2 in one lab-on-a-chip device. The sample channel for each chip in the stack may have an associated sample inlet and gas opening. Also, each sample channel may have its own set of reagents. For example, each sample channel may have a strong acid, indicator, buffer and color shifting agent and one or more of these reagents may be different for different channels. There may be one pump for all of the channels or a separate pump for each channel.

Figure 3:
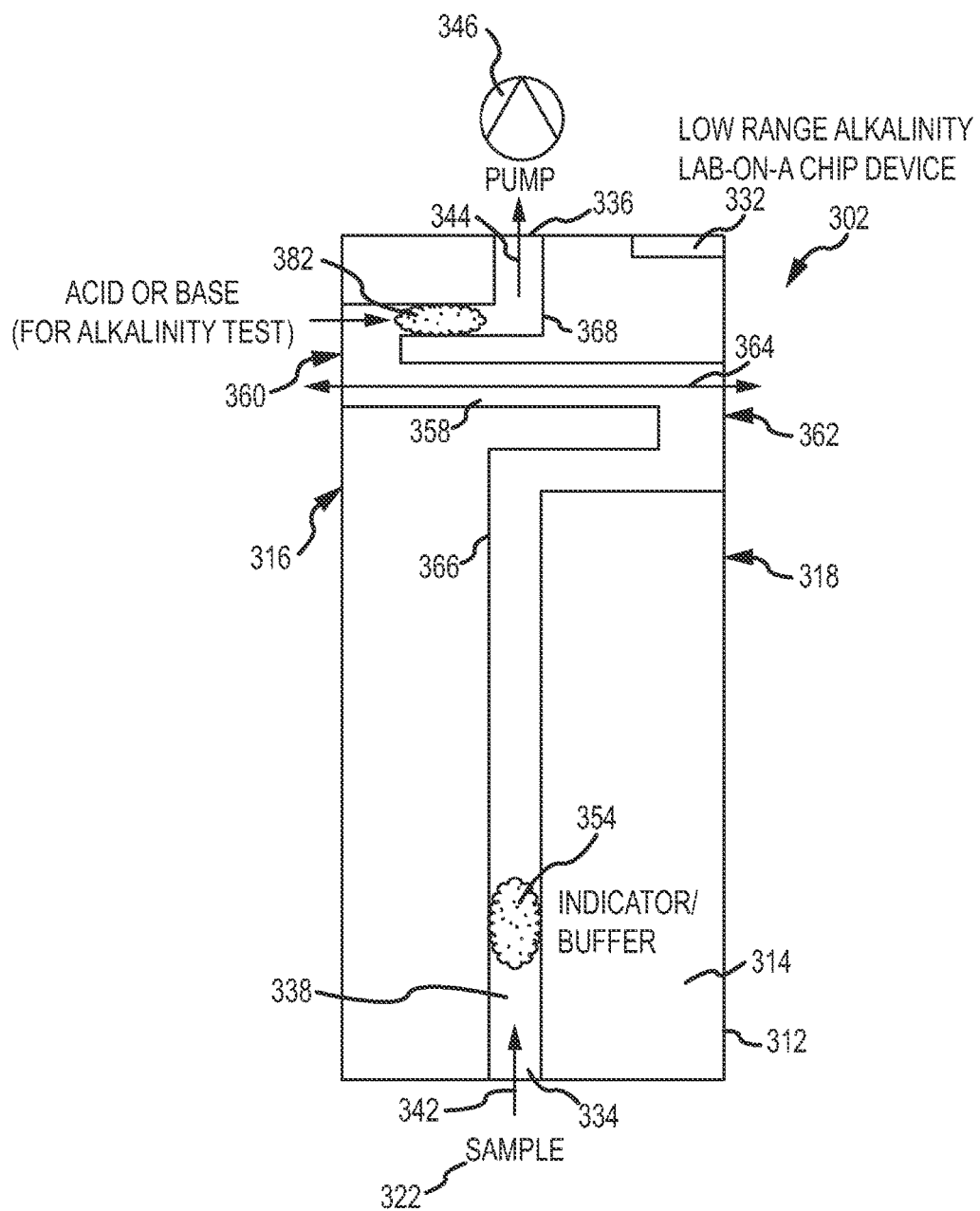
FIG. 3 is a schematic drawing of a low-range alkalinity lab-on-a-chip device and portable reader according to one embodiment of the present invention.

FIG. 3 shows a low-range alkalinity lab-on-a-chip device 302 according to one embodiment of the present invention. Lab-on-a-chip device 302 includes a chip 312 having a chip body 314 and two walls, i.e., walls 316 and 318, on either side of chip body 314. Lab-on-a-chip device 302 includes various components used in measuring alkalinity in an aqueous sample, such as aqueous sample 322. When chip 312 is inserted into a chip reader (not shown), an indent 332, i.e., an alignment interface of chip 312, interacts with a chip holding interface (not shown) of the chip reader to hold chip 312 in the chip reader when force is no longer applied to chip 312 by a user. When chip 302 is inserted into the chip reader, indent 332 aligns the optical pathway with the optical system of the chip reader. Chip 312 has a sample inlet 334 and a gas opening 336. A sample channel 338 extends between sample inlet 334 and gas opening 336. Sample channel 338 includes optical pathway 358 and two transparent windows 360 and 362 that allow light from a chip reader reading chip 312 to traverse optical pathway 358 as shown by double-headed arrow 364. Sample channel 338 also includes a pre-optical pathway portion 366 and a post-optical pathway portion 368. Although for simplicity of illustration, pre-optical pathway portion 366 and post-optical pathway portion 368 are shown in FIG. 3 as having only one (1) and two (2) bends, respectively, pre-optical pathway portion 366 and post-optical pathway portion 368 may each have several bends. Sample 322 may be pulled into sample channel 338 from a water source via capillary action or by using a pump on gas opening 336 when chip 312 is dipped into a water source or otherwise exposed to a water source. Sample 322 is pulled through sample channel 338, as indicated by arrows 342 and 344 via force exerted by a pump 346 that is part of the chip reader (not shown). Pump 346 exerts a suction force on sample 322 by pulling air from sample channel 338 via gas opening 336.

As the sample 322 is pulled through sample channel 338 by pump 346, sample 322 mixes with reagents in reagent zone 354. Reagent zone 354 includes an indicator and a buffer. Sample 322 reacts with the reagents in reagent zone 354 as sample 322 travels along sample channel 338.

Optical pathway 358 allows for the optical system of a chip reader, such as the chip reader of FIG. 1 (not shown in FIG. 3) to measure the color of sample 322 and/or one or more of the reagents. Then the sample 322 undergoes an alkalinity test, in which sample 322 mixes a color shifting agent in reagent zone 382. The color shifting reagent may be an acid or a base. The pumping of sample 322 through sample channel 338 may be stopped and/or the direction of pumping reversed to allow absorbance to be measured in optical pathway 358 by the chip reader after sample 322 mixes with the color shifting agent in reagent zone 382. The chip reader then displays the results to a user on a display.

In the embodiment of the invention shown in FIG. 3, there are two transparent windows, i.e., transparent windows 360 and 362 at either end of optical pathway 358. In this embodiment, light from the chip reader is directed through window 360 and the characteristics of the light are measured by the optical system of the chip reader when the light exits window 362. In another embodiment of the present invention, window 360 of FIG. 3 may be replaced with a mirror or a mirrored wall. In this embodiment, the chip reader may emit a light through window 362 along optical pathway 358 that is reflected back by the mirror or mirrored wall back along pathway and back through window 362 and into the optical system of the chip reader.

Although for simplicity of illustration in FIG. 3 only one sample channel with an associated sample inlet, gas opening, and pump are shown for each lab-on-a-chip device, a lab-on-a-chip device may have multiple sample channels. This may be accomplished by stacking multiple chips of the type shown in FIG. 3 in one lab-on-a-chip device. The sample channel for each chip in the stack may have an associated sample inlet and gas opening. Also, each sample channel may have its own set of reagents. For example, each sample channel may have an indicator, buffer and color shifting reagent and one or more of these reagents may be different for different channels. There may be one pump for all of the channels or a separate pump for each channel.

Figure 4:
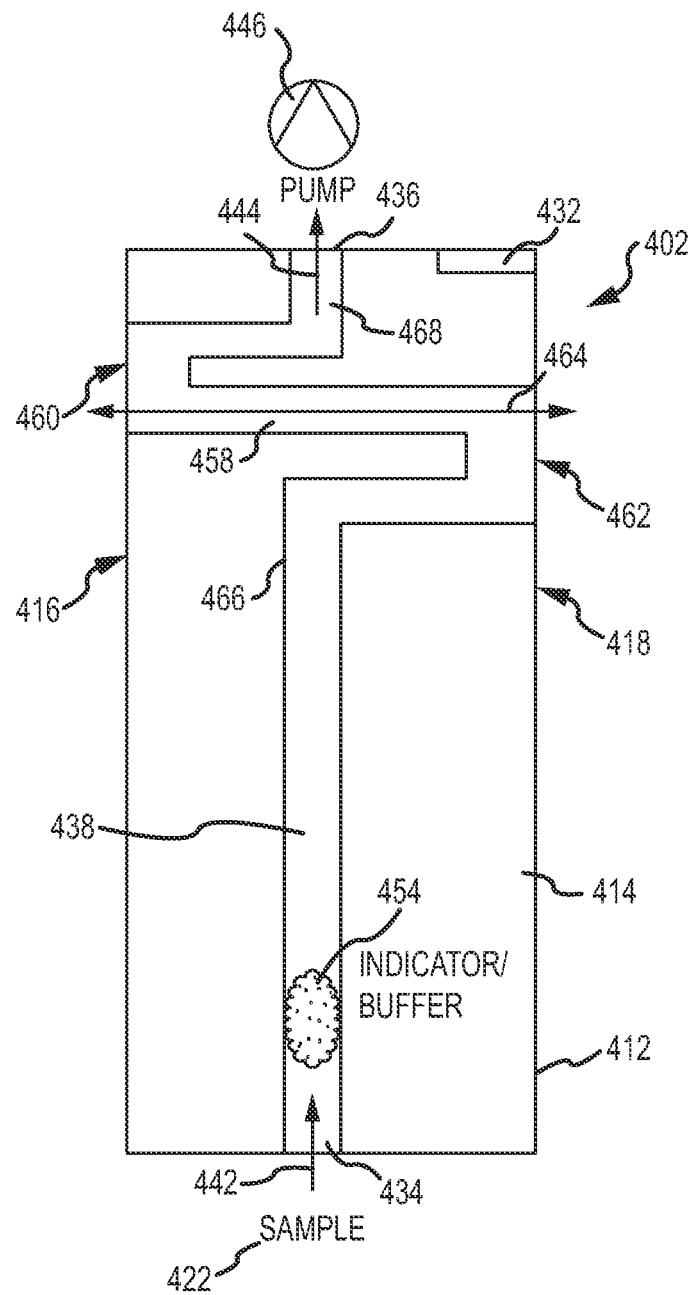
FIG. 4 is a schematic drawing of an alkalinity lab-on-a-chip device that includes only an indicator and buffer according to one embodiment of the present invention.

FIG. 4 shows a lab-on-a-chip device 402 according to one embodiment of the present invention. Lab-on-a-chip device 402 includes a chip 412 having a chip body 414 and two transparent walls, i.e., walls 416 and 418, on either side of chip body 114. Lab-on-a-chip device 402 includes various components used in measuring alkalinity in an aqueous sample, such as aqueous sample 422. When chip 412 is inserted into a chip reader (not shown), an indent 432, i.e., an alignment interface of chip 412, interacts with a chip holding interface (not shown) of the chip reader to hold chip 412 in the chip reader when force is no longer applied to chip 412 by a user. When chip 402 is inserted into the chip reader, indent 432 aligns the optical pathway with the optical system of the chip reader. Chip 412 has a sample inlet 434 and a gas opening 436. A sample channel 438 extends between sample inlet 434 and gas opening 436. Sample channel 438 includes optical pathway 458 and two transparent windows 460 and 462 that allow light from a chip reader reading chip 412 to traverse optical pathway 458 as shown by double-headed arrow 464. Sample channel 438 also includes a pre-optical pathway portion 466 and a post-optical pathway portion 468. Although for simplicity of illustration, pre-optical pathway portion 466 and post-optical pathway portion 468 are shown in FIG. 4 as only having one (1) and two (2) bends, respectively, pre-optical pathway portion 466 and post-optical pathway portion 468 may each have several bends. Sample 422 may be pulled into sample channel 438 from a water source via capillary action or by using a pump on gas opening 436 when chip 412 is dipped into a water source or otherwise exposed to a water source. Sample 422 is pulled through sample channel 438, as indicated by arrows 442 and 444 via force exerted by a pump 446 that is part of the chip reader (not shown). Pump 446 exerts a suction force on sample 422 by pulling air from sample channel 438 via gas opening 436.

As the sample 422 is pulled through sample channel 438 by pump 446, sample 422 mixes with reagents in reagent zone 454. Reagent zone 454 includes an indicator and a buffer. Sample 422 reacts with the reagents in reagent zone 454 as sample 422 travels along sample channel 438.

Optical pathway 458 allows for the optical system of a chip reader, such as the chip reader of FIG. 1 (not shown in FIG. 4) to measure the color of sample 422 and/or one or more of the reagents. The chip reader then displays the results to a user on a display.

In some embodiments of the present invention, the sample channels of FIGS. 1, 2, 3 and 4 may have multiple bends either before or after the optical pathway. These multiple bends may serve a variety of purposes including: (1) better mixing of the reagent, (2) an increase in the time the sample requires to traverse the chip, (3) an increase in bubble elimination and (4) an increase in the "bench space," or surface area, for reagent placement.

In the embodiment of the invention shown in FIG. 4, there are two transparent windows, i.e., transparent windows 460 and 462 at either end of optical pathway 458. In this embodiment, light from the chip reader is directed through window 460 and the characteristics of the light are measured by the optical system of the chip reader when the light exits window 462. In another embodiment of the present invention, window 460 of FIG. 4 may be replaced with a mirror or a mirrored wall. In this embodiment, the chip reader may emit a light through window 462 along optical pathway 458 that is reflected back by the mirror or mirrored wall back along pathway and back through window 462 and into the optical system of the chip reader.

In one embodiment of the present invention, window 460 of FIG. 4 may be replaced with a mirror or a mirrored wall. In this embodiment, the chip reader may emit a light along optical pathway 458 that is reflected back into the chip reader by the mirror or mirrored wall.

Although for simplicity of illustration in FIG. 4 only one sample channel with an associated sample inlet, gas opening, and pump are shown for each lab-on-a-chip device, a lab-on-a-chip device may have multiple sample channels. This may be accomplished by stacking multiple chips of the type shown in FIG. 4 in one lab-on-a-chip device. The sample channel for each chip in the stack may have an associated sample inlet and gas opening. Also, each sample channel may have its own set of reagents. For example, each sample channel may have an indicator and buffer combination and one or more of these reagents may be different for different channels. There may be one pump for all of the channels or a separate pump for each channel.

According to one embodiment of the present invention, the sample may be inserted into the sample channel of the chip either before or after the chip is inserted into or otherwise connected to a chip reader.

Although in FIGS. 1, 2, 3 and 4 the two transparent windows are formed by the portions of two transparent walls that are not blocked by the chip body, in other embodiments of the present invention, the two transparent windows may be windows that are inserted into openings in the chip body.

Although for simplicity of illustration there is only one strong acid, one indicator and one buffer shown in FIGS. 1, 2, 3 and 4, the lab-on-a-chip device may include multiple strong acids, indicators and buffers. One example of using two indicators, i.e., a mixed indicator system, is to use a bromocresol green-methyl red indicator system as the indicator.

Although for simplicity of illustration, there is one only one optical pathway shown in the sample channel of FIGS. 1, 2, 3 and 4, a sample channel may include multiple optical pathways to allow a color change to be measured by a chip reader after various reagents are mixed with the aqueous sample being analyzed.

When a mixed indicator system comprising a first indicator and a second indicator is employed in the lab-on-a-chip device, a dual wavelength measurement may be taken by the chip reader. The ratio of the absorbance of one color (base form) to a second color (acid form) of the first indicator to the ratio of the absorbance of one color (base form) to a second color (acid form) of the second indicator may be utilized to obtain a value related to the alkalinity of the sample.

The reagents used in the reagent zones may be dry, liquid, or a mixture of phases. Reagents may be present as gels, solids, crystals, etc.

In one embodiment of the present invention, a buffer and an indicator of known amounts and composition are reacted with a known volume of sample on a lab-on-a-chip device. The buffer/indicator undergoes color transition more broadly when interacting with alkalinity than occurs in a traditional strong acid titration for alkalinity determination. This is a result of a weak acid (i.e., the buffer on the chip device) and weak bases in the sample (due to the presence of carbonates and bicarbonates, for example). FIG. 5 shows an example of a weak acid-weak base titration curve. The buffer on the chip is of a pH that is just below the desired endpoint (e.g., pH 8.0 for P-Alkalinity determination or pH 4.0 for total alkalinity determination). The addition of a sample containing alkalinity shifts the pH of the buffered indicator to higher pH values and consequently shifts the color of the indicator as well. If the buffer and buffer capacity are chosen appropriately, the color change occurs slowly over a large alkalinity range. In this way, the extent of the color transition can be related to the concentration of the alkalinity in the sample.

Figure 6:
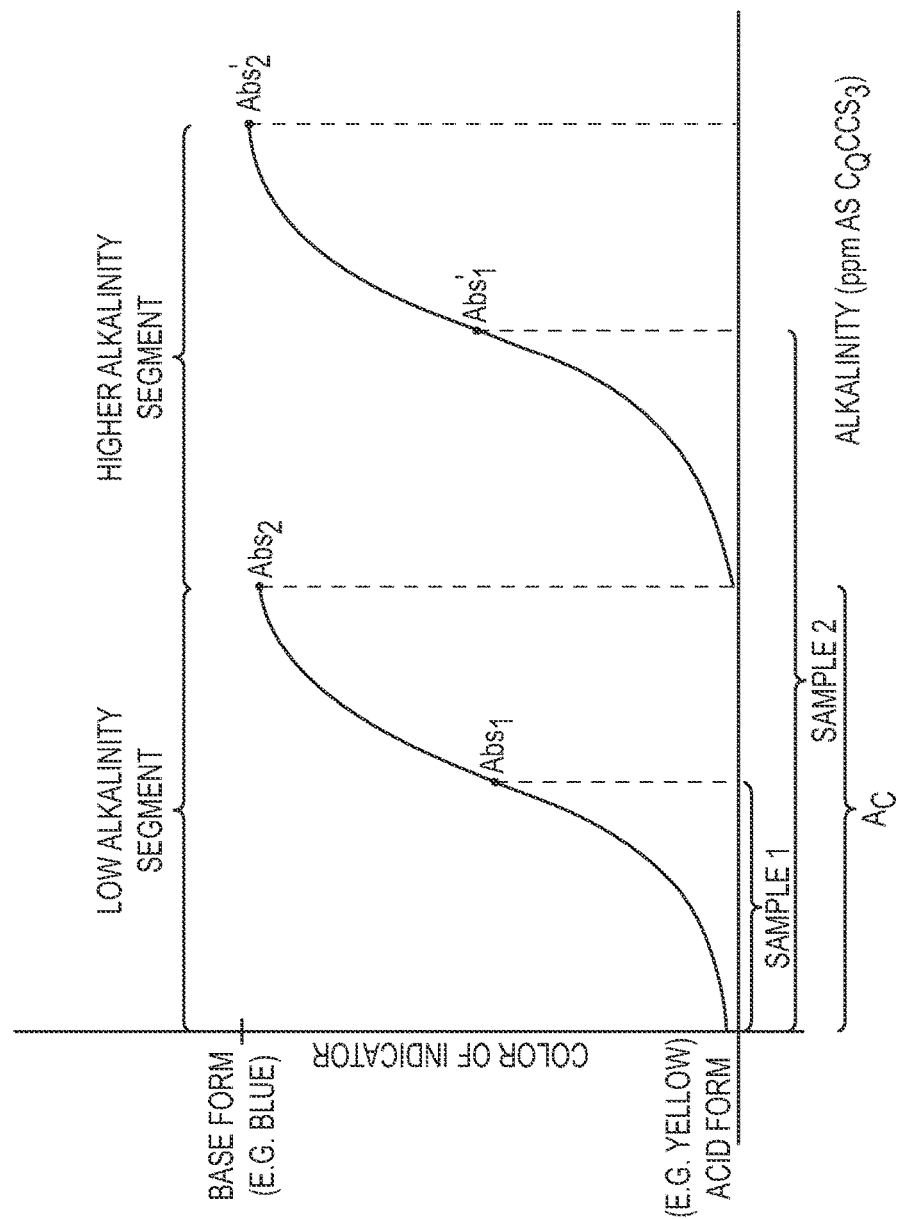
FIG. 6 is a graphical representation of the methods by which alkalinity may be determined according to one embodiment of the present invention.

In one embodiment of the present invention, lab-on-a-chip device 302 of FIG. 3 may be used in the following manner. Sample 322 is pulled into chip 312 via a pumping mechanism or capillary action. Sample 322 is pulled through sample channel 338 via the force from pump 346. In reagent zone 352, a buffer and an indicator, i.e., two reagents, are mixed with sample 322. Sample 322 is then pulled into optical pathway 358 which allows for the optical system of the chip reader (not shown in FIG. 3) to make a first measurement of the color of the sample and the reagents. The extent of the color change is dependent upon the concentration of alkalinity in sample 322 and the pH and buffer capacity of the indicator and buffer reagents. Sample 322 is then pulled further along sample channel 338 into reagent zone 382 where an excess of a color shifting reagent, i.e., one or more acids or bases, is mixed with sample 322 to shift the color of sample 322 to at least one color extreme. The pumping of sample 322 through sample channel 338 is then reversed and the sample is forced back into the optical pathway 358, which allows for the optical system of the chip reader to make a second measurement of the color of sample 322 and the reagents. The optical system of the chip reader transmits the sample data to a display that is part of the chip reader or part of a separate visual display device, thereby displaying the data to a user. The data may either be in a raw form or in a manipulated form that is more easily understood by a user. A ratio of the two measurements is used to determine the alkalinity in the sample and reduces errors caused by variations in the indicator reagent for chip 302. FIG. 6 demonstrates this graphically for a system using a shift to a full base color. The alkalinity is determined by the Equation 2 below:

$$[\text{Alkalinity}]=(\text{Abs}_1/\text{Abs}_2)\times(\text{Calibration factor})$$

$$[\text{Alkalinity}]=ax^2+bx+c \quad \text{(Equation 2)}$$

where, $x=(\text{Abs}_1/\text{Abs}_2)$

In one embodiment of the present invention, lab-on-a-chip device 202 may be used in the following manner to make a higher range measurement of alkalinity of an aqueous sample. Aqueous sample 222 is pulled through sample channel 238 via the force from pump 246. Sample 222 encounters a strong acid in reagent zone 252 and then an indicator and a buffer in reagent zone 254. The strong acid neutralizes a predetermined quantity of alkalinity. Utilization of a strong acid in this fashion allows for a measurement of a higher segment of alkalinity concentrations. This is graphically shown in FIG. 6. The measurement range by this method then spans from the concentration of the alkalinity consumed by the first strong acid reagent ($A_C$), plus the range of alkalinity measurable by the color transition of the buffered indicator. FIG. 5 shows a standard strong acid and weak base titration curve in the steepness of change upon the addition of alkalinity. The weak acid-weak base shows the more gradual change with added alkalinity. This gradual change gives better resolution to the measurement in the application of this technique.

After reacting with the first strong acid, indicator, and buffer reagents, sample 222 is then forced into optical pathway 258 wherein the optical system of the chip reader (not shown) makes a first measurement of the color of the sample and reagents. The extent of the color change is dependent upon the concentration of alkalinity in the sample. The sample is then forced further along the channel and encounters an excess of at least one acid or base, as a color shifting agent, in reagent zone 282 to shift the color of sample 222 to at least one color extreme. The sample is then forced into optical pathway 258, by reversing the pumping direction of pump 246, which allows for the optical system of the chip reader to make a second measurement of the color of the sample 222 and reagents. A ratio of the two measurements reduces variations in the indicator in the sample chip. The optical system of the chip reader transmits the sample data to a display that is part of the chip reader or part of a separate visual display device, thereby displaying the data to a user. The data may either be in a raw form or in a manipulated form that is more easily understood by a user. Using the ratio method as explained in Equation 2 above, one can determine the alkalinity of the higher range sample by Equation 3:

$$[\text{Alkalinity}]=A_C+(\text{Abs}_1/\text{Abs}_2)\times(\text{Calibration factor}) \quad \text{(Equation 3)}$$

Figure 7:
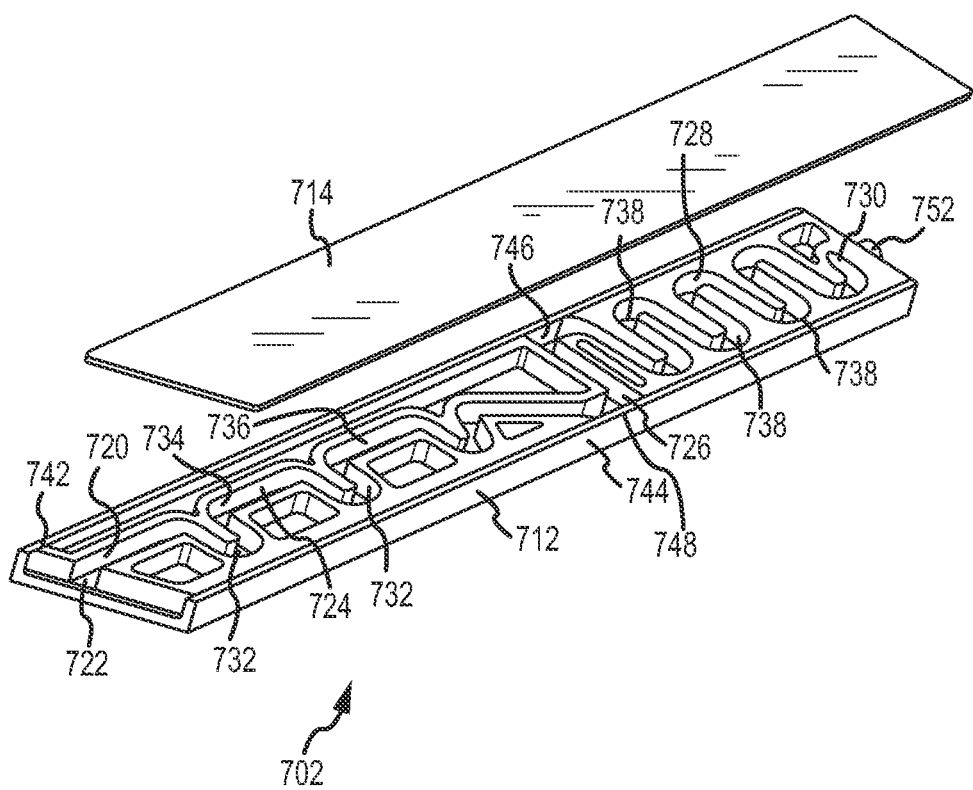
FIG. 7 is an exploded view of a chip design, according to the present invention.

FIG. 7 shows a lab-on-a-chip device 702 according to one embodiment of the present invention. Lab-on-a-chip device 702 includes a chip 712 and a cover 714. Chip 712 includes a sample channel 720 having an inlet 722, a pre-optical pathway portion 724, an optical pathway 726 and a post-optical pathway portion 728, and a gas opening 730. Pre-optical pathway portion 724 includes bends 732 between which are reagent zones 734 and 736, in which reagents (not shown) may be placed. Post-optical pathway portion 728 includes bends 738. Bends 732 and 738 allow for the movement of a sample (not shown) through channel 720 to be more easily controlled, allow for enhanced mixing and provide a longer path-length for the channel on a small chip. Chip 712 includes two transparent walls 742 and 744 that form respective opposing aligned windows 746 and 748, respectively, of optical pathway 726. When cover 714 is placed on chip 712, channel 720 is closed except for inlet 722 and gas opening 730. Clip 752 holds chip 712 in a slot in a chip reader not shown by physical force, for example, tension applied by the slot on the instrument against chip body.

The cover of FIG. 7 may be held on the chip by any conventional means, such as by an adhesive, welding, a force fit, UV bonded, or any other means of connecting two pieces of plastic, etc.

A multi-chip lab-on-a-chip device may be made by stacking devices of the type shown in FIG. 7 on top of each other and then adhering the chips together by any conventional means such as an adhesive, welding, UV bonded, or any other means of connecting two pieces of plastic.

Figure 8:
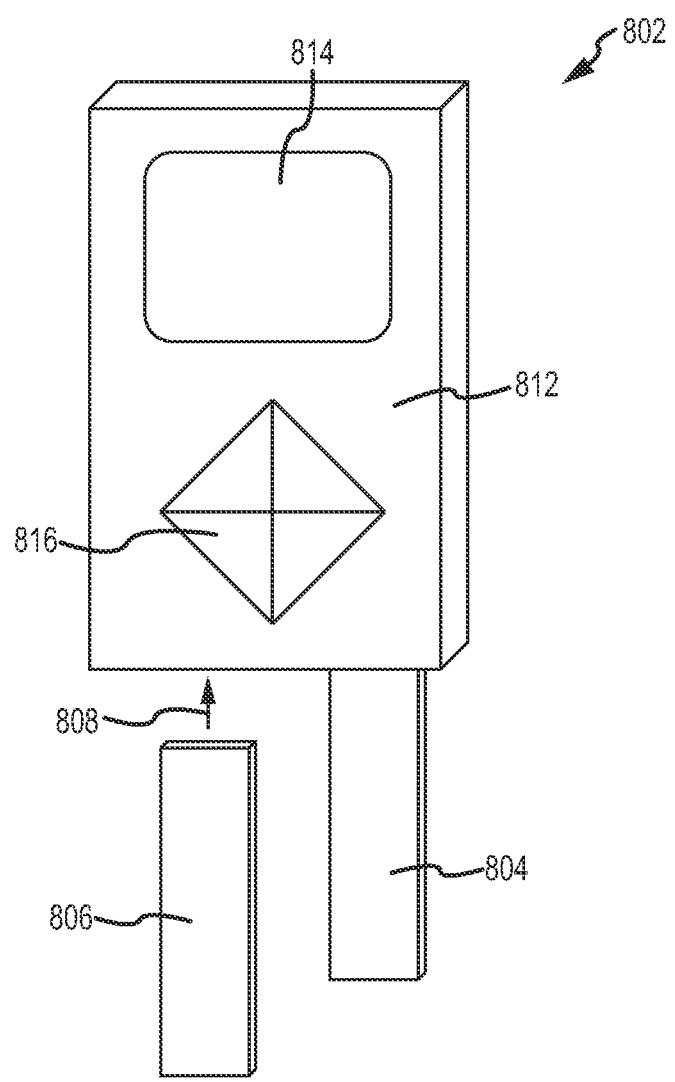
FIG. 8 is a drawing that shows an alkalinity chip(s) interfacing with the reader and display according to one embodiment of the present invention.

FIG. 8 shows a chip reader 802 according to one embodiment of the present invention into which a first lab-on-a-chip device 804 has been inserted into a first slot (not visible in FIG. 8) in chip reader 802 in order to be read by optical system (not visible in FIG. 8) of chip reader 802. A second lab-on-a-chip device 806 is about to be inserted into a second slot (not visible in FIG. 8) in chip reader 806 as indicated by arrow 808. Chip reader 802 includes a body 812 in which are mounted a display 814 and controls 816.

Although in the embodiment of the present invention shown in FIG. 8, the control and display are on the chip reader, in other embodiments of the present invention the display and controls may be part of a separate device that is remote from the chip reader and in wired or wireless communication with the chip reader.

Figure 9:
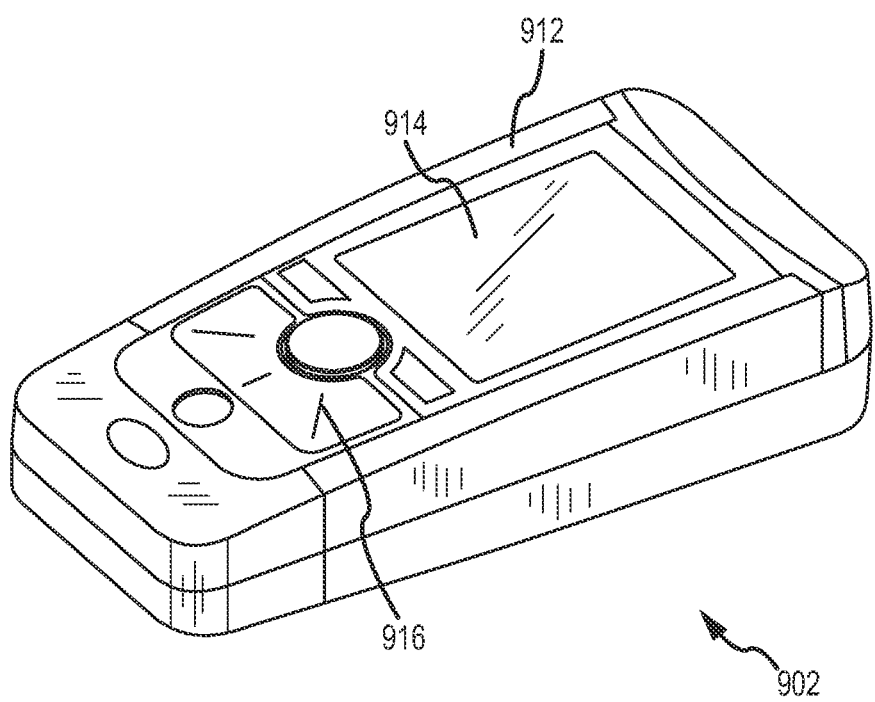
FIG. 9 is a perspective view of a chip reader according to one embodiment of the present invention.

FIG. 9 shows a chip reader 902 according to one embodiment of the present invention. Chip reader includes a body 912 in which are mounted a display 914 and controls 916.

Figure 10:
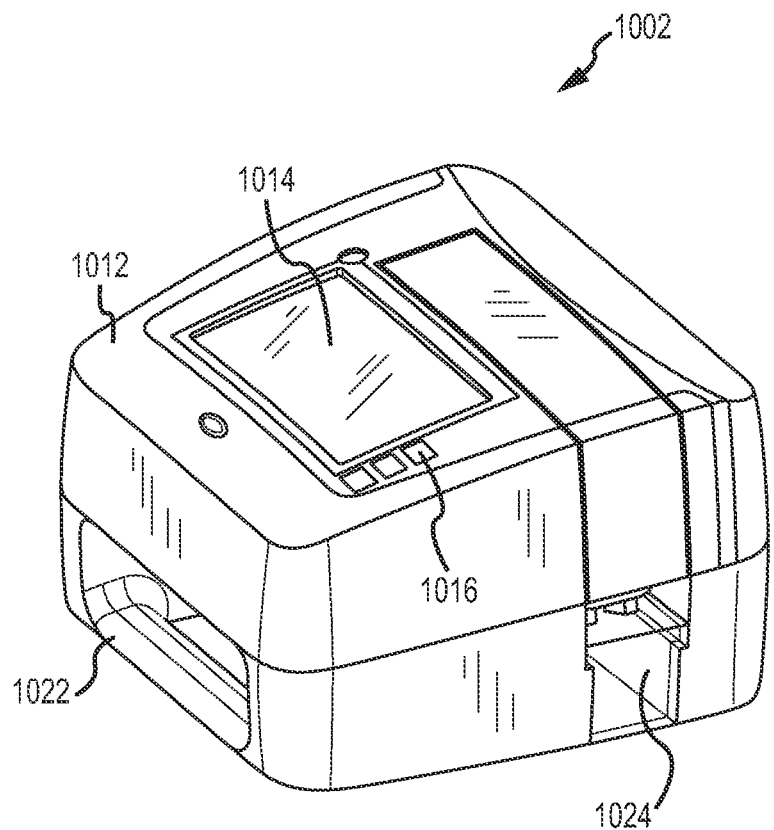
FIG. 10 is a perspective view of a laboratory reader according to one embodiment of the present invention.

FIG. 10 shows a chip reader 1002 according to one embodiment of the present invention. Chip reader includes a body 1012 in which are mounted a display 1014 and controls 1016.

Figure 11:
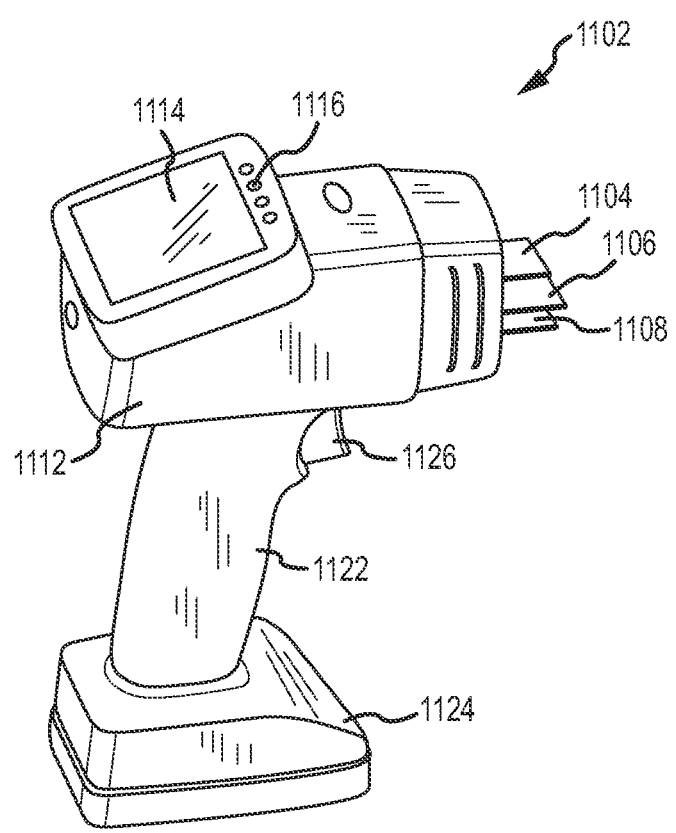
FIG. 11 is a perspective view of a handheld reader and alkalinity lab-on-a-chip devices according to one embodiment of the present invention.

FIG. 11 shows a chip reader 1102 according to one embodiment of the present invention into which three lab-on-a-chip devices, i.e., lab-on-a-chip devices 1104, 1106 and 1108 have been inserted into respective slots (not visible in FIG. 11) in chip reader 1102 in order to be read by optical system (not visible in FIG. 11) chip reader 1102. Chip reader 1102 includes a body 1112 in which are mounted a display 1114 and controls 1116. Chip reader 1102 includes a handle 1122 and a power supply 1124. Mounted on handle 1122 is a trigger 1126 for manual start of measurement and/or manual ejection of chips.

Figure 12:
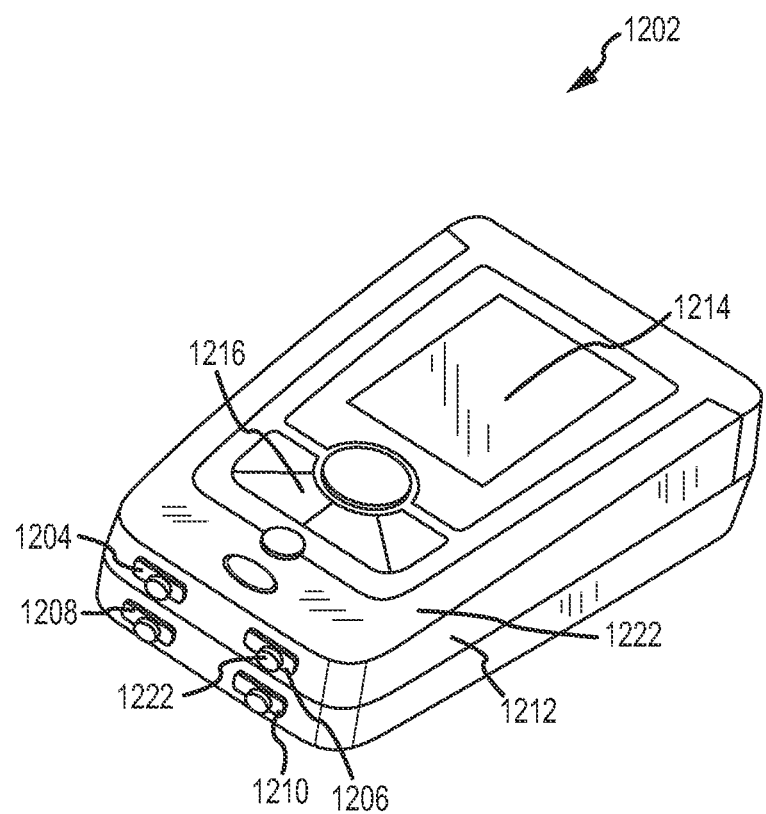
FIG. 12 is a perspective view of a pocket, or handheld, reader according to one embodiment of the present invention.

FIG. 12 shows a chip reader 1202 according to one embodiment of the present invention into which four lab-on-a-chip devices, i.e., lab-on-a-chip devices 1204, 1206, 1208 and 1210 have been inserted into respective slots (not visible in FIG. 12) in chip reader 1202 in order to be read by optical system (not visible in FIG. 12) of chip reader 1202. Chip reader 1202 includes a body 1212 in which are mounted a display 1214 and controls 1216. Also, the chip has a inlet dust and moisture cover 1222.

FIG. 13 shows a method of calculating the alkalinity as a means of absorbance according to one embodiment of the present invention. FIG. 13 shows calculation of alkalinity as a function of absorbance values obtained during measurement. These calculations take into account variations in chemical depositions and composition.

Figure 14:
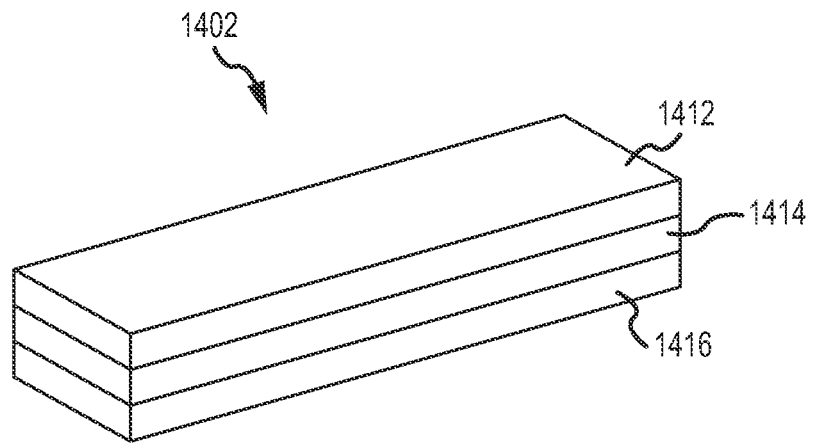
FIG. 14 is a perspective view of a lab-on-a-chip device comprising multiple chips in a stacked configuration.
Figure 15:
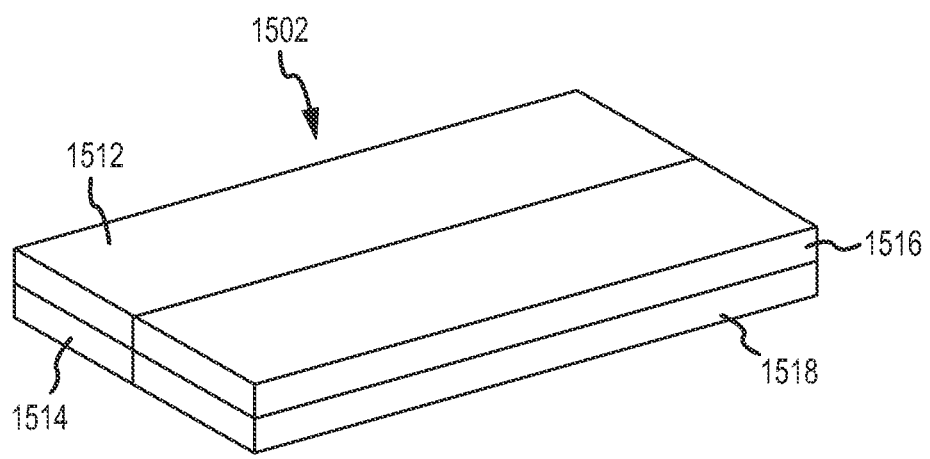
FIG. 15 is a perspective view of a lab-on-a-chip device comprising multiple chips in a side-by-side stack configuration.

A lab-on-chip device of the present invention may comprises multiple chips arranged in stacks, arranged side-by-side, or arranged in any other configuration. FIG. 14 shows a lab-on-a-chip device 1402 according to one embodiment of the present invention comprising multiple chips. Lab-on-a-chip device 1402 includes a stacked configuration that includes three chips, i.e., chips 1412, 1414 and 1416 configured in combination. In another embodiment, a lab-on-a-chip device may be a conjugated configuration, such side-by-side stack configuration shown in FIG. 15 that includes a plurality of chips configured in combination as shown in FIG. 15. FIG. 15 shows a lab-on-a-chip device 1502 that includes four chips, i.e., chips 1512, 1514, 1516 and 1518 arranged in a side-by-side stack configuration. Although in FIGS. 14 and 15, the chips on the lab on a chip devices are shown as being adjacent to each other, in other embodiments of the present invention, the chips may be separated from each other by other structures for various purposes such as to provide easier access to sample inlet, to provide easier access to the gas opening, to allow the chips to be read by a particular reader, etc.

In the claims, unless specified otherwise, steps of a method may be performed in any order. For example, in a method claim, step (b) may be performed before step (a), unless the language of the claim requires that step (a) be performed prior to step (b).

Having described many embodiments of the present invention, it will be apparent that modifications, variations, alterations and changes are possible without departing from the full scope of the present invention as defined in the appended claims, and equivalents thereof. It should be appreciated that all examples in the present disclosure, while illustrating many embodiments of the present invention, are provided as non-limiting examples and are, therefore, not to be taken as limiting the various aspects so illustrated.

Detailed embodiments of the present invention are disclosed herein; however, it is to be understood that the disclosed embodiments are merely exemplary of the present invention that may be embodied in various forms. It will be appreciated that many modifications and other variations are within the intended scope of this invention as claimed below. Furthermore, the foregoing description of various embodiments does not necessarily imply exclusion. For example, "some" embodiments may include all or part of "other" and "further" embodiments within the scope of this invention.

What is claimed is:

1. A method comprising the following steps:
    (a) forcing, using a pump integrated into a chip reader, an aqueous sample through a sample channel in a chip to mix the aqueous sample with one or more reagents located in one or more reagent zones of the sample channel and thereby forming a mixture that exhibits a color change due to an interaction of one or more reagents with a constituent of the aqueous sample and/or with a selected one or more of the one or more reagents, wherein the sample channel comprises a pre-optical pathway portion and a post-optical pathway portion and wherein at least one of the pre-optical pathway portion and the post-optical pathway portion comprises a plurality of bends of the sample channel,
    (b) measuring a color change in the mixture in a traverse optical pathway in the sample channel, the traverse optical pathway extending the width of the chip and having at least one transparent window on at least one side thereof; and
    (c) displaying data on a visual display device based on the color change measured in step (b).

2. The method of claim 1, wherein step (b) is performed by a chip reader and wherein the visual display device is part of the chip reader.

3. The method of claim 1, wherein step (b) is performed by a chip reader and wherein the method comprises the following steps:
    (d) producing measured data based on the color change measured in step (b), and
    (e) transmitting the measured data to the visual display device using a wireless communication link, wherein the displayed data is based on the measured data.

4. The method of claim 1, wherein step (b) is performed by a chip reader in which the chip is inserted.

5. The method of claim 1, wherein the one or more reagents comprise one or more indicators.

6. The method of claim 1, wherein the one or more reagents comprise one or more strong acids.

7. The method of claim 1, wherein a selected one or more of the reagents are dry.

8. The method of claim 1, wherein the method comprises the following step:
    (d) using a first reagent of the one or more reagents to consume a known amount of analyte in the aqueous sample to thereby modify a range of analyte determination.

9. The method of claim 1, wherein step (a) comprises the following steps:
- (d) mixing the aqueous sample with an indicator to form an aqueous sample-indicator mixture, and
- (e) mixing a color shifting agent with the aqueous sample-indicator mixture to form a color-shifted mixture.

10. The method of claim 1, where the method comprises using a continuous color transition gradient to determine the alkalinity of the aqueous sample based on the color change measured in step (b).

11. The method of claim 1, wherein step (b) comprises the following steps:
- (d) directing light through a first window at a first end of the optical pathway to traverse the optical pathway, and
- (e) measuring light exiting a second window at second end of the optical pathway.

12. The method of claim 1, wherein step (b) comprises the following steps:
- (d) directing light through a window at a first end of the optical pathway to traverse the optical pathway,
- (e) reflecting the light back along the optical pathway when the light reaches a mirror at a second end of the optical pathway, and
- (f) measuring light reflected back along the optical pathway when the reflected light exits the window.

\* \* \* \* \*